(12) United States Patent
Berrevoets et al.

(10) Patent No.: US 10,695,104 B2
(45) Date of Patent: *Jun. 30, 2020

(54) ADJUSTABLE FIXATION DEVICE

(71) Applicant: Pioneer Surgical Technology, Inc., Marquette, MI (US)

(72) Inventors: Gregory Berrevoets, Big Lake, MN (US); Frankie Morris, Austin, TX (US); Frederick E. Finger, Cornelius, NC (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/119,946

(22) Filed: Aug. 31, 2018

(65) Prior Publication Data

US 2019/0008563 A1 Jan. 10, 2019

Related U.S. Application Data

(63) Continuation of application No. 14/974,843, filed on Dec. 18, 2015, now Pat. No. 10,064,661, which is a continuation of application No. 13/710,058, filed on Dec. 10, 2012, now Pat. No. 9,216,042.

(60) Provisional application No. 61/569,064, filed on Dec. 9, 2011.

(51) Int. Cl.
*A61B 17/70* (2006.01)
(52) U.S. Cl.
CPC ...... *A61B 17/7055* (2013.01); *A61B 17/7002* (2013.01); *A61B 17/7059* (2013.01)

(58) Field of Classification Search
CPC . A61B 17/7002; A61B 17/70; A61B 17/7001; A61B 17/7007; A61B 17/7014; A61B 17/7019; A61B 17/7023; A61B 17/7025; A61B 17/7029; A61B 17/7032; A61B 17/70341; A61B 17/7041; A61B 17/7044; A61B 17/7046; A61B 17/7049; A61B 17/7055; A61B 17/7059; A61B 17/80
USPC .................................. 606/246–289
See application file for complete search history.

(56) References Cited

U.S. PATENT DOCUMENTS

| | | | |
|---|---|---|---|
| 7,618,443 B2 | 11/2009 | Abdou | |
| 7,901,433 B2 | 3/2011 | Forton | |
| 9,216,042 B2 * | 12/2015 | Berrevoets | A61B 17/7055 |
| 9,381,044 B2 * | 7/2016 | Robinson | A61B 17/7052 |
| 10,064,661 B2 * | 9/2018 | Berrevoets | A61B 17/7055 |
| 2002/0049446 A1 | 4/2002 | Harkey | |
| 2002/0120268 A1 | 8/2002 | Berger | |
| 2003/0153913 A1 | 8/2003 | Altarac | |
| 2005/0288669 A1 | 12/2005 | Abdou | |

(Continued)

*Primary Examiner* — Pedro Philogene
(74) *Attorney, Agent, or Firm* — Fitch, Even, Tabin & Flannery LLP

(57) ABSTRACT

An articulated fixation device is provided having a high degree of adjustability for securing a plate member thereof to a skull and at least one spinal rod thereof to a vertebral bone. In one form, an adjustable bridge member is provided that is adjustably connected to both the plate member and the spinal rod. The adjustable connections can include an upper and rearward pivot connection between the plate member and the bridge member and a lower and forward pivot connection between the spinal rod and the bridge member.

17 Claims, 8 Drawing Sheets

(56) References Cited

U.S. PATENT DOCUMENTS

| | | | |
|---|---|---|---|
| 2006/0217710 A1* | 9/2006 | Abdou | A61B 17/6433 |
| | | | 606/54 |
| 2007/0118121 A1* | 5/2007 | Purcell | A61B 17/7058 |
| | | | 606/261 |
| 2007/0233119 A1 | 10/2007 | Markworth | |
| 2008/0051783 A1* | 2/2008 | Null | A61B 17/7055 |
| | | | 606/261 |
| 2009/0270924 A1 | 10/2009 | Wing | |
| 2011/0190824 A1 | 8/2011 | Gephart | |
| 2012/0078306 A1* | 3/2012 | Lynch | A61B 17/705 |
| | | | 606/264 |

* cited by examiner

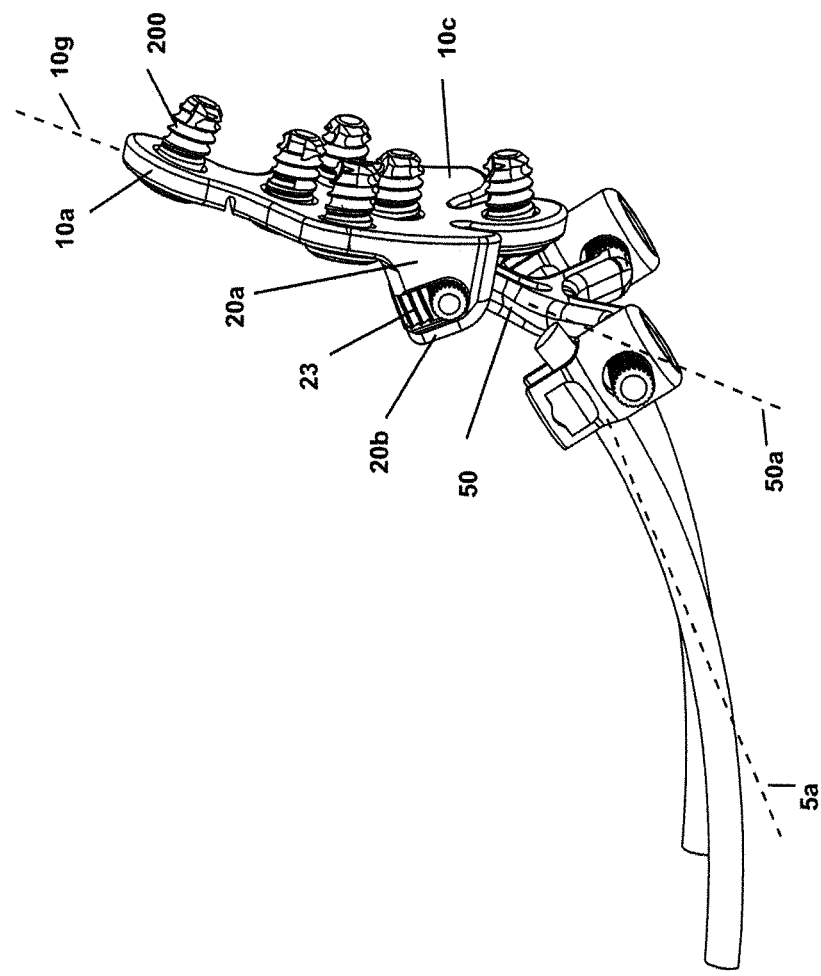

ADJUSTABLE FIXATION DEVICE

CROSS REFERENCE TO RELATED APPLICATIONS

This application is a continuation of U.S. patent application Ser. No. 14/974,843, filed Dec. 18, 2015, which is a continuation of U.S. patent application Ser. No. 13/710,058, filed Dec. 10, 2012, now U.S. Pat. No. 9,216,042, which claims the benefit of U.S. Provisional Application No. 61/569,064 entitled "Adjustable Occipital Plate Device" filed Dec. 9, 2011, which are all hereby incorporated herein by reference in their entirety.

FIELD OF THE INVENTION

The invention relates generally to devices for securing the ends of spinal rods or other elongate fixation members to the skull of a patient for spinal repair and/or fusion surgeries.

BACKGROUND OF THE INVENTION

Rigid or semi-rigid elongate members, such as spinal rods, may be mounted to the spinal column in order to stabilize or immobilize vertebrae of the spinal column for a variety of purposes. For instance, spinal rods are often secured to adjacent vertebral bodies via anchor members in order to promote fusion of the two vertebrae as a treatment for degenerative disc disease, spondylolisthesis, spinal stenosis, fractures of the vertebrae, and other conditions. Limiting or preventing motion of the vertebrae promotes the healing process. By removal of the disc positioned between the vertebrae and limiting motion between the vertebrae, the adjacent boney surfaces are allowed to grow into one another and fuse together. Fusion devices may also be placed between the two immobilized vertebrae in order to facilitate the process of fusion.

When stabilizing portions of the spinal column, and in particular the cervical region of the spine, it is sometimes necessary to immobilize the skull in addition to vertebrae. The same elongate rigid structures used to link and stabilize the vertebrae may therefore be secured to the skull in order to keep the skull in an appropriate spatial relationship with respect to the spinal column. However, since the anatomy and thickness of the skull and its surrounding tissues are very different than those of the vertebrae and their surrounding tissues, the elongate rigid structures must be anchored to the skull in a different manner than that used for the vertebrae.

For instance, in many spinal stabilization procedures elongate rods made of titanium or other materials are placed adjacent to the posterior side of the spine and anchored in place using screws connected to some type of coupling assembly. Examples of coupling assemblies for posterior fixation systems are disclosed in U.S. Pat. No. 7,141,051; U.S. Published Application No. 2008/0045955; and U.S. Published Application No. 2007/0225711. The screws used to anchor these devices and other coupling assemblies are often relatively long, and are mounted to the pedicle area of the vertebrae with the shanks of the screws penetrating deep into the vertebral body. The yoke portion or receiving member of the coupling assembly that is coupled to the screw and receives the spinal rod is nested between outwardly-extending boney processes so that the height of the yoke is not noticeable.

When spinal rods are mounted to the skull, however, it is undesirable to use long screws and large coupling assemblies. Many coupling assemblies also would prove unduly cumbersome if mounted directly to the skull, and may even protrude significantly from the back of the head. In addition, the occipital region, which juts out at the base of the skull, typically is the site at which to mount an internal fixation system, requiring that spinal rods connected thereto be severely bent in order to be positioned along the occipital region and be connected to the occipital region in a manner similar to the connection to the vertebrae.

Previous systems for coupling spinal rods and other elongate stabilization devices to the skull vary. However, most systems utilize a plate mounted to the occipital region of the skull that attaches to a rod, cable, wire, plate, or screw mounted to a region of the spine. In most spinal rod systems, two spinal rods are positioned generally parallel to the surface of the plate and then secured thereto by a bracket, yoke, or other receiving member, such as a U-shaped receiving member. The plates are mounted to the skull with several small screws disposed along the full length and width of the plate. Since the base of the skull angles inward toward the spine, the plates mounted to the skull are not parallel to the posterior surfaces of the vertebrae, and the spinal rods must be bent significantly away from the vertebrae in order to reach the occipital region in an orientation so that they may be mounted to the plate. For instance, the bending of spinal rods in order for them to properly be received relative to an occipital plate is shown in the devices of FIGS. 1, 2, and 18 of U.S. Published Application No. 2004/0153070. In that device, spinal rods mounted along the vertebrae must be manipulated in order to fit precisely into receiving mechanisms aligned along the sides of a plate designed to be fixed to the occipital region of the skull. This bending of the rod can fatigue the rod material, and also makes it difficult to reposition the elements of the stabilization system.

Even attempts to provide occipital plate devices with adjustability in order to accommodate spinal rods of various orientations still generally require significant manipulation and bending of spinal rods before they can be secured to the plate structure. For instance, U.S. Pat. No. 6,902,565 discloses a plate designed to be mounted to the occipital region of the skull by a plurality of short expansion head screws. The plate receives a pair of rods that may be further mounted to one or more vertebrae. In many cases these rods are pre-bent so that the majority of the rods may be positioned parallel to the spine, with the ends bent transversely in order to be secured to the plate by a clamp plate or bracket. Some embodiments include plates that are bent in order to receive the rods that are parallel to the spine.

U.S. Published Application No. 2008/0051783 discloses a plate device having a pair of u-shaped rod receiving members that protrude from lateral wings of the plate. The wings may be shifted laterally and medially, and the rod receiving members may rotate to adjust the direction in which a connecting member (such as a spinal rod) is received. The spinal rods must be positioned so that they are generally parallel to the plate surface in order to fit into the rod receiving members. Therefore, the ends of the rod must be bent away from the axis of the spine, which is not parallel to the plate surface, and into the u-shaped channels of the receiving members.

U.S. Pat. No. 6,524,315 discloses a plate secured to the bone by a plurality of screws. The plate is fitted with slotted bolts designed for receiving a rod or cable. The base of the slotted bolt is recessed in the plate at its base. A support platform may be fitted over the bolt to help hold the rod or cable. A nut fastens over the threaded end of the slotted bolt to trap the rod or cable within the bolt, securing it to the plate. The bolt may be rotated to adjust the direction of the rod or cable.

U.S. Published Application 2007/0233119 discloses a plate device with polyaxial connector head assemblies including a connector body that receives a spinal rod and a connector head pivotably connected to the connector body and configured to be secured to the plate so that the connector assemblies provide limited polyaxial movement of the spinal rods with respect to the plate. However, the coupling heads are relatively bulky and still hold the spinal rods relatively parallel to the plate surface.

Even more adjustable occipital plates have various shortcomings. In U.S. Published Application 2007/0118121, a fixation plate includes a laterally extending arm coupled to a pair of spinal rods by sliding links that are able to slide along and pivot about the arms. However, ends of the spinal rods are held relatively close to the fixation plate, and positioning of the sliding links is limited to sliding and pivoting along the fixed laterally extending arms. Further, the sliding links are locked in place by clamping together top and bottom portions thereof with a set screw positioned at a distance from the laterally extending arm, which compresses a rounded portion of the link about the arm in order to inhibit sliding. However, the locking force between the sliding links and the laterally extending arms may not be able to prevent pivoting or sliding of the spinal rods relative to the fixation plate when sufficient force is applied.

U.S. Pat. No. 7,901,433 also discloses an adjustable occipital plate system that permits spinal rods to be positioned at various angles with respect to the plane of the occipital plate. The horseshoe-shaped plate has a lateral arm extending from each side, with a variable connector securing each spinal rod to a lateral arm of the plate system. A gap separates the two lateral arms, and may allow some twisting of the plate arms and spinal rods. In addition, the horseshoe-shape of the plate may not allow all of the bone screws to be driven into the thickest and hardest bone which is typically in the central area of the occipital region of the skull. The horseshoe-plate of the '433 patent also will have to be bent because of its substantially flat configuration and the non-flat or curved configuration of the skull's occipital region. Bending of the relatively narrow, curved arms of the plate will undesirably further weaken the plate. Additionally, bending the plate and the rods involves trial-and-error and, as such, is typically a very time consuming process. This is particularly challenging with these types of occipital plate and spinal rod assembles where during surgery, the patient's occiput and cervical vertebrae are typically oriented one way relative to each other with the patient supported on an operating table, and need to be oriented another way relative to each other for final fixation of the assembly to the occiput and the cervical vertebrae. The connectors of the '433 patent hold the spinal rods below or even with the lateral arms, and thus relatively close to the spine. However, this can create interference with the cervical vertebrae immediately below the occiput (i.e., the C1 and C2 vertebrae), and potentially the brain stem where it may be exposed due to damage to surrounding bone.

SUMMARY OF THE INVENTION

Fixation devices are provided herein for mounting to bone and receiving one or more spinal rods. The devices may offer the ability to receive spinal rods in various orientations without requiring significant bending, if any, of the spinal rods. For instance, the devices may allow for adjustment of the angle of the rod or other connecting member with respect to the surface of the occipital plate device, and may allow multiple types of movement and adjustability for a highly articulated device. Typically, these systems include a plate member that is curved to generally conform to the surface of the skull and particularly the occipital region or occiput thereof, or another boney region. The fixation devices also have coupling devices that include coupling members or rod receiving members for coupling elongate connecting members, such as spinal rods, to the plate member, with the coupling members configured to have multiple degrees of adjustability in order to accommodate elongate connecting members of various configurations and orientations relative to the plate member. The adjustable coupling devices allow the fixation or plate device to secure spinal rods of various configurations and orientations without significantly bending the spinal rods, thus avoiding unnecessary stress and fatigue on the rods. Although the devices may be configured to secure a variety of elongate connecting members, such as rods, cables, wires, and the like, spinal rods will be primarily discussed herein. It will be understood, however, that this description is not intended to be limiting, and that the invention is intended to be adapted for use with a variety of connecting members of different shapes, sizes, and configurations.

The plate devices disclosed herein are optimally configured to receive and hold spinal rod members over prior art plate devices configured for mounting to the occipital region of the skull, and may secure spinal rods having different orientations, configurations, and spacing without requiring bending of the rods. The plate devices provided herein have improved adjustability and/or are more easily implanted and locked to fix the spinal rods in place when compared to the prior art. The plate devices can be adapted by a surgeon to lock spinal rods without significant bending of the rods. Prior art devices which require spinal rods to be bent to fit properly to the occipital place can fatigue the rods, potentially resulting in breakage of the rod and failure of the spinal stabilization system.

In certain forms, the occipital devices described herein include a relatively flat plate member configured to be secured to a patient's occiput, and are secured to a pair of spinal rods through adjustable coupling devices. Although the plate member is relatively flat, it need not be planar, and preferably has a slight curvature at least along its engagement surface with the skull to substantially match the surface curvature of the occipital region of the skull. The plate member may include a plurality of apertures for receiving anchor members that secure the plate member to the skull. The plate may also be provided with grooves or notches at particular points along its surface in order to enhance the bendability of the plate or to allow certain portions of the plate to be removed if unneeded.

More particularly, in one form, the plate member has a compact configuration particularly in the lateral direction or generally in a transverse plane along the base of the skull. In this regard, the plate member has a main plate body portion that can have a generally polygonal configuration, albeit with some curvature along the perimeter thereof, so that there are no gaps in the main body portion beyond apertures therein for fasteners to secure the plate member to the skull. One such configuration can be a pentagonal configuration, for instance. With its compact configuration, the plate member herein is able to be secured to the central area of the occipital region where the greatest purchase with the fasteners can be achieved in the thickest and hardest bone of the occiput.

In another form, the compact plate member has a plurality of apertures for fasteners that are generally aligned along the longitudinal axis of the fixation device or in a coronal plane. The longitudinally aligned apertures also assists in keeping the lateral size of the main body portion to a minimum. In one preferred form, the plate member also includes extension portions that have apertures for fasteners, and that can be aligned with the longitudinally aligned apertures. The extension portions and the main body portion have weakened or frangible portions therebetween to allow the extension portions to be bent or removed from the plate member so that the size of the plate member can also be adjusted, such as in the longitudinal direction, to accommodate anatomical variations in the occipital regions of different patients.

The plate member may be coupled to a modular bridge portion or member that is adjustable with respect to the plate, with the adjustable connection being generally toward the lower longitudinal end of the plate member and toward the upper longitudinal end of the bridge member. A pair of coupling devices or yoke devices may be adjustably connected to the bridge member in order to receive spinal rods which can extend in various directions without requiring significant bending of the spinal rods, which can cause fatigue and failure of the spinal rods. The adjustable connections between yoke devices, and thus the spinal rods, and the bridge member is preferably generally toward the lower longitudinal end of the bridge member and toward the upper longitudinal ends of the spinal rods. With the bridge member adjustably connected to the plate member, and to the spinal rods via the adjustably connected coupling devices, the bridge member has longitudinally spaced adjustable connections to the plate member and the spinal rods such that the fixation device has an articulated structure with adjustable connections that are spaced in the longitudinal and fore-and-art directions when the device is implanted. In this manner, the articulated fixation device can be secured to the occiput and the cervical vertebrae without needing to significantly bend the plate member and the spinal rods if at all.

If the bridge portion of the device is adjustable relative to the plate member such as via coupling devices and rod portions of the plate member and the bridge member, the bridge member or portion may be adjusted to a variety of orientations and then locked into place at a desired orientation. If the device includes a modular bridge portion, the plate member may be implanted before attaching the bridge portion so that the surgeon can secure the plate to the skull without the bridge portion obstructing the process. A plurality of modular bridge members of different sizes and/or configurations also may be provided, which would permit the surgeon to select different bridge portions for different patients or situations.

In one form, the plate member has a pair of rod-receiving bracket, yoke or receiver member portions integrated therewith at the longitudinal lower corner portions thereof and laterally spaced across the plate member from each other. The yoke portions have laterally extending channels for receiving laterally extending rod portions of the bridge member at the longitudinally upper end thereof. The yoke portions and the rod portions could be reversed to be formed on the bridge member and the plate member, respectively. Having the yoke portions formed integrally as one-piece with the plate member, however, is advantageous since the curved wall portions include a thickened portions of the plate body at the corner areas and curved wall portions that extend closely adjacent thereto. In this manner, the yoke portions do not project upwardly and in a cantilevered fashion from the bridge member and instead the plate member maintains its robust, compact construction even with the yoke portions integrated therewith.

In one form, the coupling devices each are configured to receive a laterally extending rod-like portion of the bridge portion of the occipital plate device so that each of the coupling devices may be pivoted about the rod portions so that the spinal rods can extend to various angles relative to the plate member, and may be shifted laterally along the rod-like portion. The positioning of each coupling device on its respective lateral arm portion may be locked by a locking device, such as a set screw, that provides a locking force in order to hold a spinal rod in place within a channel of the coupling device.

The coupling devices may also be configured to receive a compression insert for assisting in stabilizing and locking the coupling device to the lateral rod portions of the plate device bridge portion. The compression inserts may also provide a provisional hold position where sufficient holding force is applied to the lateral arm portion to minimize accidental movement of the coupling devices, but adjustment of the coupling devices is still possible when sufficient force is applied to overcome the holding force. The provisional hold provided by the coupling device allows the main components of the articulated fixation device to be adjustably secured relative to the bones including the bridge member extending between the plate member and the spinal rods with the patient supported on the operation table facing downwardly. The provisional hold allows for the angulation between the components to be adjusted as the occiput and cervical vertebral bones are adjusted to the position at which they are to be fixed and also allows the components to be exchanged for different sizes thereof before fully being locked in place.

The bridge member can also be provided with a compact, robust configuration in the lateral direction where the bridge member is adjustably connected to the plate member. More particularly, the longitudinally upper rod portion are sized to extend literally to opposite lateral ends that are laterally spaced by a smaller distance than the corresponding opposite lateral ends of the lower rod portions. Thus, the longitudinally upper adjustable connection is maintained close to the longitudinal axis of the device or sagittal plane where the anchoring of the plate member to the occiput is strongest.

Plate devices also may be provided with fixed bridge portions that are not adjustable relative to the plate body. Regardless of whether the bridge portion is modular or fixed, the bridge may be arched in order to provide clearance for avoiding contact with the vertebral processes and connective tissue of the spine.

BRIEF DESCRIPTION OF THE DRAWINGS

FIG. 2A is a perspective view of the device showing the curved configuration of the plate member engagement surface.

DETAILED DESCRIPTION OF PREFERRED EMBODIMENTS

The plate devices disclosed herein are optimally configured to receive and hold spinal rod members than prior art plate devices configured for mounting to the occipital region of the skull, and may secure spinal rods at various positions and orientations without requiring significant bending of the rods or the plate members, if at all. The plate devices provided herein have improved adjustability and/or are more easily locked to fix the spinal rods in place when compared to the prior art.

One embodiment of a device 2 including an occipital plate member with adjustable coupling devices or members for receiving spinal rods is shown in FIGS. 1-4. The illustrated device includes a relatively flat plate member 10 configured to be secured to the patient's skull and secured to a pair of spinal rods 5 through adjustable couple coupling devices 70. Although the plate member is relatively flat, it need not be planar, and preferably has a slight curvature to match the surface of the occipital region of the skull.

Figure 1:
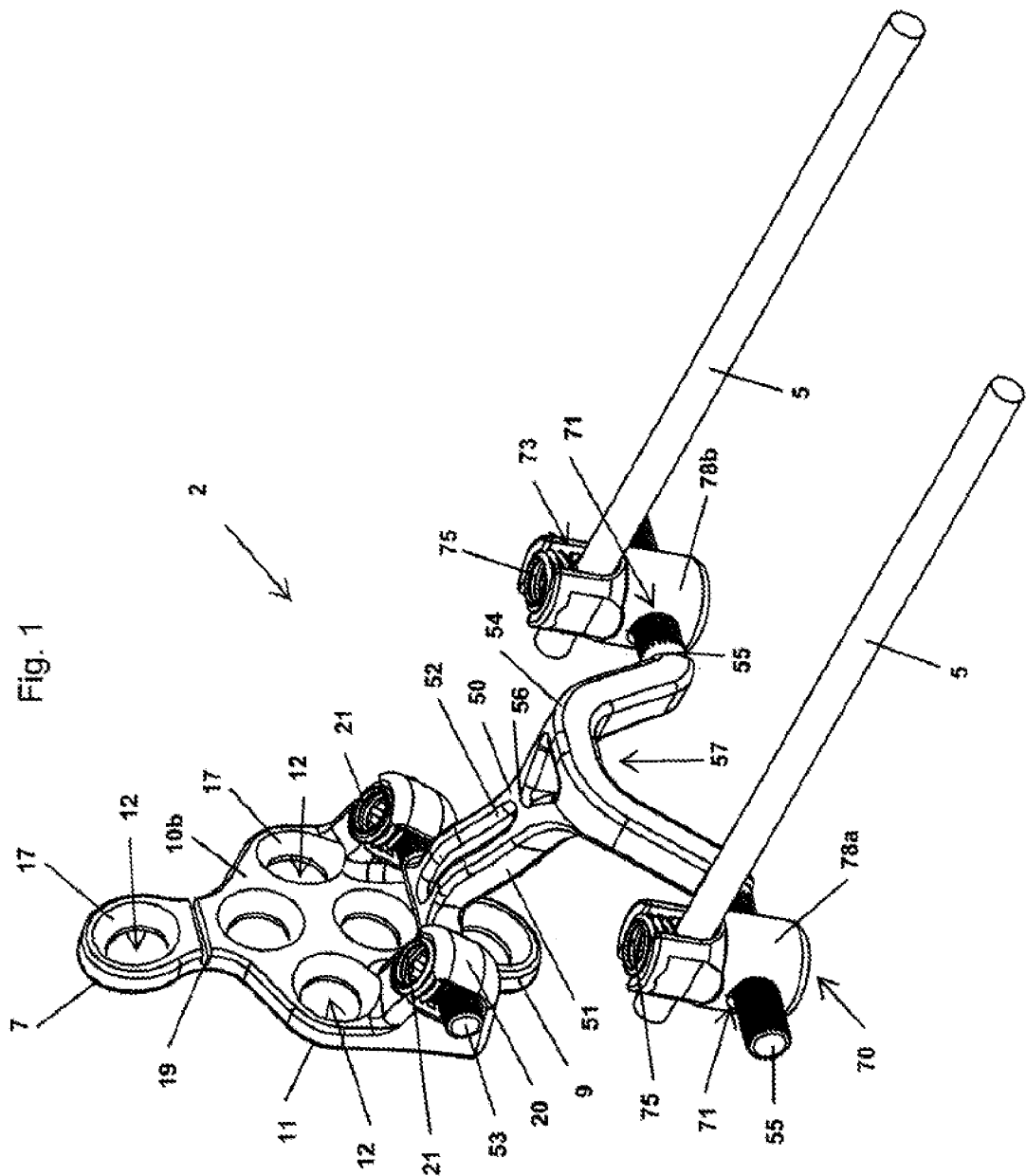
FIG. 1 is a perspective view of one form of an occipital plate device according to the present invention having a modular bridge member adjustable and coupled to an occipital plate member and a pair of spinal rods.
Figure 2:
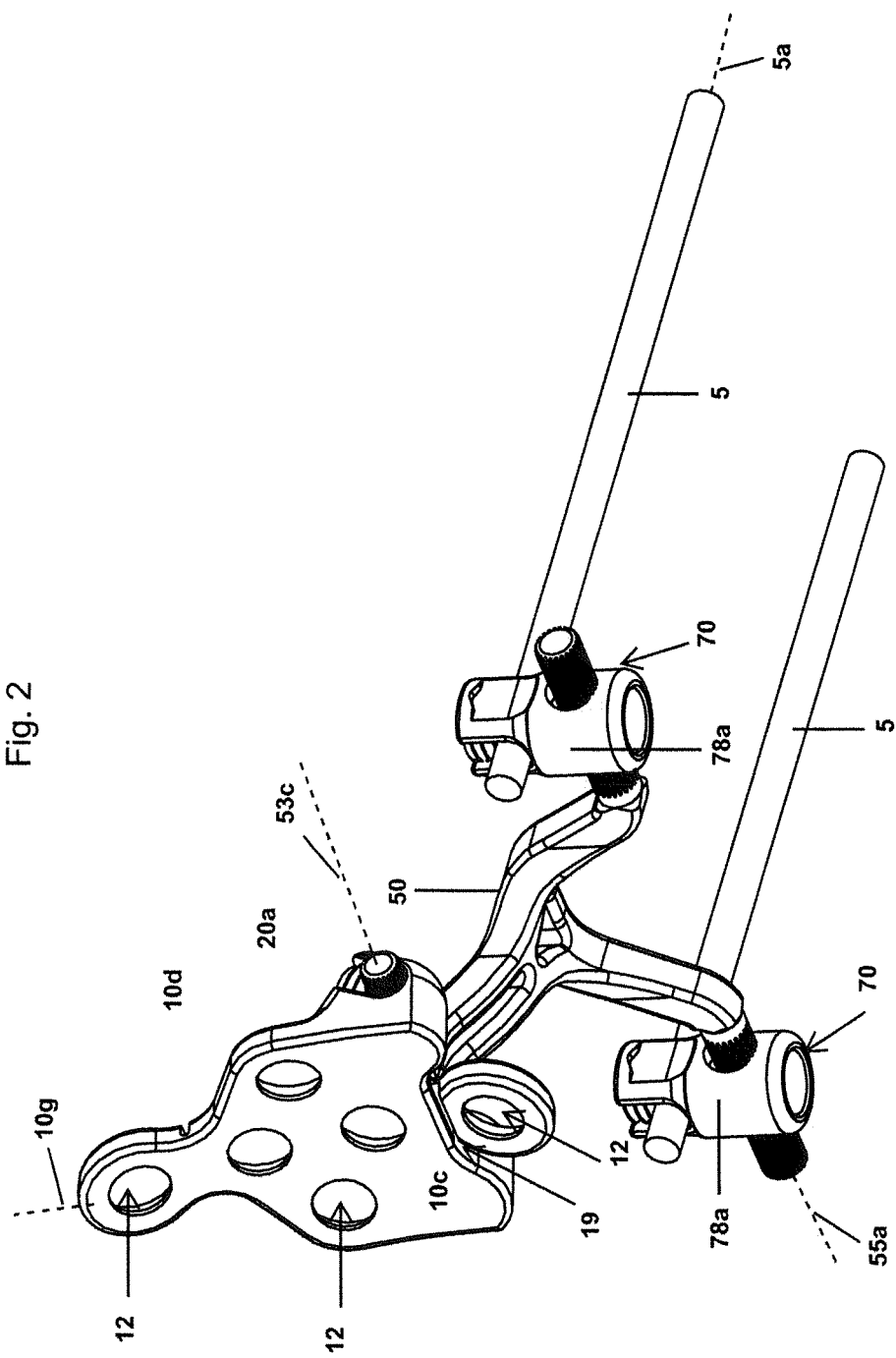
FIG. 2 is a perspective view of the device from FIG. 1 from the rear, showing the engagement surface of the plate member that will be mounted to a patient's skull.

As shown in FIGS. 1 and 2, the plate member 10 has a plate body 10a that includes opposite surfaces 10b and 10c, and a main body portion 10d which includes a plurality of apertures 12 for receiving anchor members that secure the plate member 10 to the skull. The surface 10c is an engagement surface for being engaged against the skull. In this regard, the engagement surface 10c can have a curved, concave configuration for conforming to the convexly curved occipital region of the skull. The main body portion 10d has a compact configuration in the lateral direction between opposite lateral edges 10e and 10f so that the plate member 10 can be secured to the central thickness and hardest area of the occiput. By way of example, the lateral distance between the edges 10e and 10f is approximately 1.025 inches. The main body portion can have a generally polygonal configuration although the perimeter edges can include curvature thereto. Several of the apertures 12 can be aligned along the longitudinal axis 10g so that the fasteners or bone screws 200 are driven into the hardest and thickness central portion of the occiput generally along the sagittal plane. The apertures 12 may have tapered surfaces in order to center the anchor members disposed therein. For instance, the rim surface 17 surrounding each aperture may be curved or beveled in order to form a spherical or conical seating surface for the head of an anchor or bone screw member. The plate 10 may also be provided weakened or frangible portions such as in the form of grooves or notches 19 at particular locations such as along its surface 10b in order to enhance the bendability of the plate at those locations in order to better match the curvature of the skull. The plate member 10 may also be cut along grooves 19 to reduce the plate size if upper lobe portion 7 or lower lobe portion 9 are not needed. As illustrated, the lobe portions 7 and 19 are centrally arranged to be aligned along the longitudinal axis 10g along with apertures 12 formed therein.

As illustrated in FIGS. 1-4, the plate member 10 may be adjustably coupled to a bridge portion or member 50 on which the pair of rod receiving coupling devices or yoke devices 70 are adjustably mounted, such as by being slidably and pivotably arranged thereon. In this manner, the device 2 is highly articulable due to adjustable connections provided between the plate member 10, the intermediate bridge portion or member 50, and the coupling devices or members 70 that receive the spinal rods 5. The spinal rods 5 can be either straight or provided with a slight curvature (FIG. 2A) to generally extend along longitudinal axis 5a. The spinal rod axis 5a and plate axis 10g generally extend in a sagittal planes and transverse to one another. Herein, when the device 2 is implanted the term longitudinal or longitudinal direction generally will be in directions in a sagittal plane and generally along the longitudinal axes of the main components of the articulated device 2 described herein, e.g., the axes 5a of the spinal rods 5, the axis 10a of the plate member 10, and the axis 50a of the bridge member 50 (see FIG. 2a). Accordingly, the adjustable connections of the articulated device 2 are longitudinally spaced and include a generally longitudinally upper adjustable connection between the plate member 10 and the bridge member 50 and a generally longitudinally lower adjustable connection between the plate member 10 and the spinal rods 5 longitudinally spaced from the upper adjustable connection generally in a sagittal plane with upper adjustable connection also being posterior to the lower adjustable connection since plate member 10 when implanted will also extend rearwardly from the spinal rods 5 and bridge member 50. More specifically, when the device 2 is implanted and locked in place, the upper connection is disposed above and rearwardly relative to the lower connection that is below and forwardly of the upper connection. This is because the plate member 10 is secured to the occiput at the base of skull that projects rearwardly from the spinal column to which the spinal rods 5 are anchored.

The bridge member 50 shown in FIG. 1 includes a cross bar 53 having laterally extending end portions 53a and 53b that can generally be rod-shaped and are adjustably held in laterally extending and upwardly open channels 23 of a pair of generally yoke or U-shaped rod receiving portions or mounting brackets 20 of the plate member 10 and secured in the channels 23 by set screws 21 engagable with internal threads of the mounting brackets 20. The yoke portions 20 each include diametrically opposite curved wall portions 20a and 20b formed at the longitudinal lower and laterally opposite corner areas of the plate body 10a. The wall portion 20a is formed by a thickening of these corner areas of the plate body 10a while the wall portion 20 extends closely adjacent thereto spaced by the channel 23 therefrom. The bridge member 50 may be pivoted about upper and rearward lateral axis 53c defined by the rod portions 53a and 53b to a variety of orientations and shifted laterally along the axis 53c with respect to the plate member 11 while the set screws 21 are positioned loosely in the mounting brackets 21, but tightening of the set screws 21 clamps the bar end portions 53a and 53b in the brackets 21 to fix the position and orientation of the bridge member 50 with respect to the plate 11.

The bridge member 50 also includes a pair of central beams 51 and 52 that join the cross bar 53 to a laterally extending portion 57 including laterally extending arms 55 that can generally be rod-shaped and upon which the adjustable coupling devices 70 are adjustably mounted. Connecting the cross bar 53 mounted to the plate 11 with the lateral portion 57 by two or more beams 51, 52 helps to resist torsion and bending of the bridge member 50 versus use of just a single beam. The beams 51, 52 may be further stabilized by providing one or more linkages or brace member 56 extending laterally between and rigidly connected to the beams 51, 52.

The coupling devices 70 associated with the bridge member 50 have outer coupling bodies or yoke members 78 that include annular wall portions 78a in which diametrically opposed through openings 71 are formed through which the laterally extending arms 55 of bridge member 50 extend. The illustrated lateral arm portions 55 are generally cylindrical or rod-shaped to allow the coupling devices to pivot, permitting them to receive spinal rods 5 of various configurations. Shifting of the coupling devices 70 medially and laterally along the lower lateral axis 55a defined by the laterally extending arms 55 permits the distance between the spinal rods 5 to be adjusted, and independent pivoting of the coupling devices 70 about the lateral axis 55a their respective laterally extending arms 55 permits orientations of the coupling devices 70 to be individually adjusted to accommodate their respective spinal rods 5. The positioning of each coupling device 70 on the arms 55 is locked by a set screw 75 that clamps the spinal rod 5 in place within an upwardly open transverse channel 73 of the coupling device 70. The laterally extending portion 57 may form an arch 54 between the coupling devices 70 in order to provide clearance space 57a for vertebral protuberances and connective tissue of the spine between the outer arms 55.

Thus, the articulated device 2 herein including the modular bridge member 50 pivotally coupled to the plate member 10 and the spinal rods 5 via the coupling devices 70 has a pair of pivot axes 53c and 55a that are spaced along the sagittal plane from each other to provide the device 2 a high degree of adjustability between the plate member 10 and the spinal rods 5. This high degree of adjustability is beneficial in allowing the articulated device 2 to be more readily and easily used with patients of varying anatomy and conditions without requiring significant bending of its components, if any, including the spinal rods 5 and the plate member 10.

Figure 3:
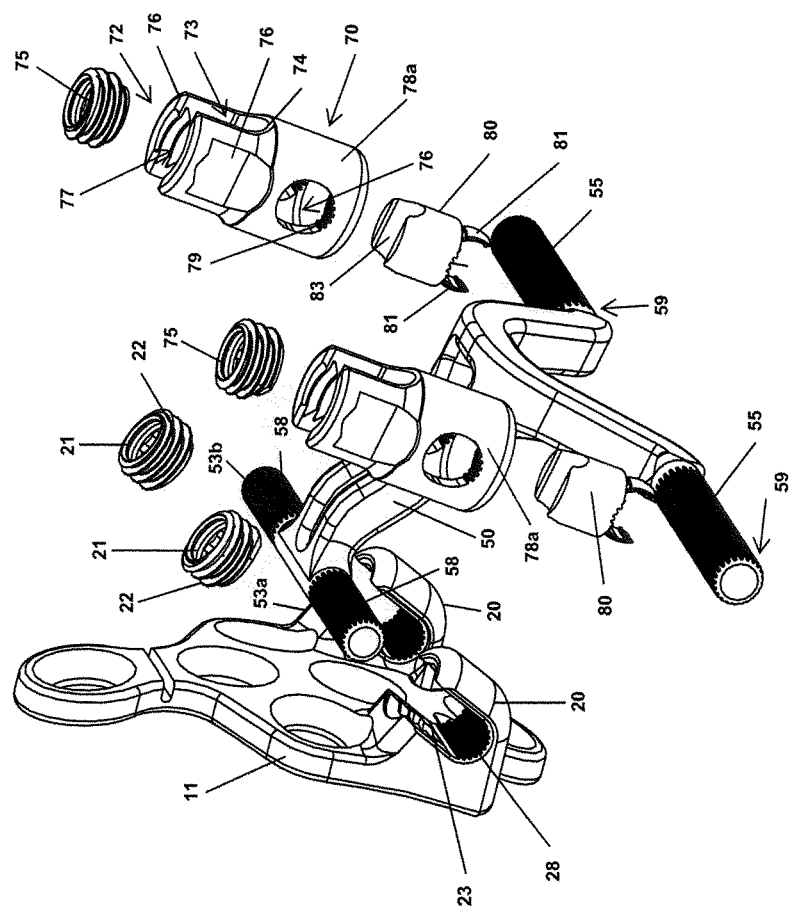
FIG. 3 is an exploded view of the device of FIGS. 1 and 2 showing the modular bridge member and coupling devices separated from the plate member.
Figure 4:
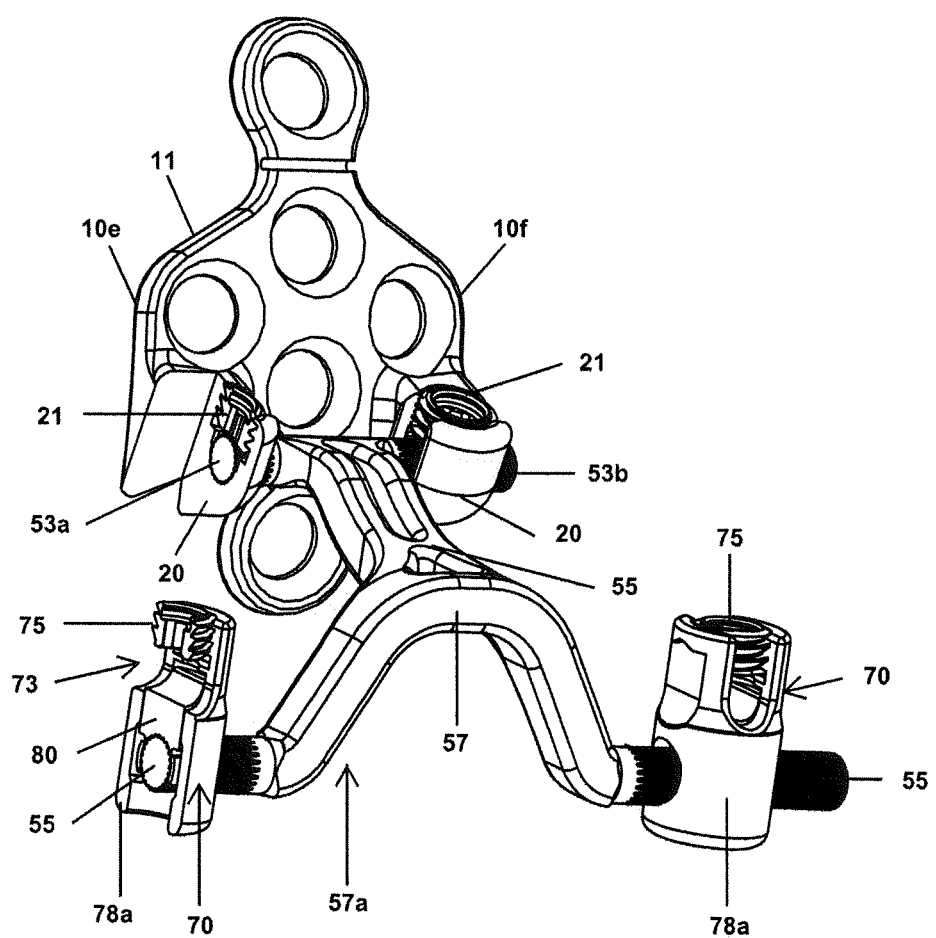
FIG. 4 is a perspective view including fragmentary portions of the coupling devices to show the locking of the coupling devices to the bridge member and bracket portions of the plate device to the bridge member.

The yoke members 78 may be U-shaped members with upright arms 76 that extend upwardly from the base portion 78a to form the transverse channel 73 therebetween sized and configured to receive a spinal rod 5, as best seen in FIGS. 3 and 4. The upwardly open channel 73 allows the spinal rods 5 to be lowered therein. The bottom 74 of the channel 73 at the top of one base portion 78a between the upstanding arms 76 may be curved or rounded in order to cradle the spinal rod and provide line contact with the rod, or may alternatively be of another shape or configuration. The yoke members 78 also are configured to receive a locking member such as set screws 75 that engage the upright arms 76 of the yoke member to secure the spinal rod 5 within the channel 73. In the illustrated embodiment, the interior surface of the upright arms 76 of the yoke members 78 are provided with threads 77 that interlock with complementary external threads of the set screw locking members 75. Alternatively, the coupling members 70 may be configured to receive other type of locking members, such as an external nut or one of various types of interior or exterior non-threaded locking members, including but not limited to bayonet-style locking members and the locking caps disclosed in U.S. Pat. No. 7,141,051; U.S. Published Application No. 2008/0045955; and U.S. Published Application No. 2007/0225711.

The coupling device 70 may also include a compression insert 80 for assisting in stabilizing and locking the coupling device 70 to the laterally extending arm 55. The compression insert 80 shown in FIG. 3 is inserted through an axial bore 72 extending through the center of the coupling device 70 and transverse, and more particularly orthogonal, to the channel 73 for receiving the spinal rod 5. The upper surface of compression insert may be contoured to the surface of the spinal rod 5. In the illustrated form, the compression insert contains an upper elongate concave channel 83 configured to receive the outer cylindrical surface of the spinal rod thereon. The illustrated compression insert also includes claws 81 that depend from its lower surface to grip either side of the laterally extending arm 55 of the bridge member 50, which can assist in provisionally holding the coupling devices 70 in place. Then the compression insert 80 is positioned within the axial bore 72 of the coupling device 70, a friction fit between the insert 80 and the interior of the coupling device 70 holds the insert 80 within the axial bore 72 of the coupling device 70. When the insert 80 is sufficiently advanced axially within the bore 72, it pushes against the lateral arm 55 disposed within the transverse throughbore 71, providing a light or provisional locking force to hold the position of the coupling device 70. Positioning the spinal rod within the rod channel 73 and tightening the locking cap 75 firmly fixes the position of the coupling device 70 by further pushing down on the compression insert 80, clamping the lateral arm 55 of the bridge member 50 between the lower surface portion 71a of the yoke member 88 extending about the transverse throughbore 71 and the bottom surface 80a of the compression insert 80.

In order to provide enhanced locking of the coupling device, the surfaces of the compression insert 80, base annular well portions 78a extending about the transverse through openings 71 therein, and/or lateral arm 55 may be keyed or contoured to better resist movement with respect to one another when clamped. For instance, the grooved lower arcuate surface portion 79 extending about the transverse throughbore 71, the grooved lower surface 89 of the compression insert 80, and the grooved outer surface 59 of the lateral arm 55 of the device 2 of FIG. 3 interlock when the compression insert 80 clamps the lateral arm 55 against the lower grooved surface portion 79 extending about the transverse throughbore 71, causing resistance to pivoting or rotation of the coupling device 70 adjacent the arms 55. When the locking cap 75 is disengaged or only lightly engaged with the spinal rod 5 extending through the yoke member 78, the light lock of the compression member may still allow some pivoting of the coupling device 70, and the grooved surface features will provide tactile feedback to the user as the coupling device is pivoted. When the locking cap 75 is fully advanced in the axial bore into tight engagement with the spinal rod 5, however, the compression insert 80 is fully advanced and clamped down against the lateral arm so that grooved surfaces 59, 79, and 89 interlock and provide great resistance to pivoting of the coupling device 70.

The lateral arm 55, compression insert 80, and coupling device 70 may be configured so that when the locking cap 75 is partially tightened the components are in a provisional lock or hold configuration in which only the grooved surface 89 of the compression insert 80 engages the grooves 59 of the lateral arm 55. Further tightening of the locking cap 75 causes the spinal rod 5 to push the insert 80 downwardly which, in turn, causes the arm 55 to be pushed downward for tight engagement between the coupling device grooves 79 and the grooves 59 of the lateral arm 55. The coupling device may also be configured so that when the compression member 80 is fully advanced downward in the axial bore 72 the interior surface of the coupling device 70 urges or forces the claw portions 81 of the insert member inward, wrapping them tightly around the lateral arm 55. The claw portions 81 also may include grooves that engage the grooved surface 59 of the lateral arm 55.

The cross bar 53 pivotably coupled to the plate member 11 may also include surface features for enhanced locking. As shown in FIG. 3, the grooved surface 58 of the cross bar 53 matches the grooved surface 28 of the bracket portions 20 of the plate member 11. When the locking devices 21, for example set screws as illustrated, are engaged with the brackets 20, the locking devices clamp the cross bar end portions 53a and 53b against the interior of the brackets 20. As the locking devices are tightened, for example by turning set screws so that their threaded exterior surfaces 22 engage the threaded interior 23 of the brackets 20, the grooved surface 58 of the cross bar will interlock with the arcuate grooved bottom surface 28 of the brackets 20, minimizing the potential rotation of the cross bar 53 relative to the plate member 10 more effectively locking the bridge portion 50 relative to the plate member 10.

Locking of the various components of the occipital plate device is further illustrated in FIG. 4. Prior to locking, the positioning of the bridge member 55 may be adjusted by pivoting the bridge member 55 about the cross rod 53 held by the brackets 20 attached to the plate body 10. Pivoting allows a surgeon to position the bridge member 50 and coupling devices 70 in a desired orientation relative to one another. The modular nature of the components also allows the surgeon to affix the plate member 10 to the patient's occiput bone without the bridge member 50 attached, reducing interference during implantation.

After the plate member 10 is properly implanted, the cross bar 53 of the bridge member 50 may be disposed in mounting brackets 20 of the plate member and provisionally coupled thereto with the locking devices 21. The modular nature of the bridge member allows the surgeon to select one of a plurality of bridge members that best fits a given patient. For instance, a kit may be provided that includes bridge members of varying lengths, and lateral widths allowing the surgeon to implant a standard plate member 11 and then select an appropriately sized bridge member for use with the current patient. After positioning the cross bar 53 in the plate's mounting brackets 20, the surgeon may pivot the bridge member 50 in order to swing the lateral arms 55 and their respective coupling devices closer to or farther away from the spinal column, as desired. It is also possible to shift the entire bridge member 50 laterally between the mounting brackets 20. Once all sagittal, coronal, and medial-lateral adjustments have been made and the bridge member has been properly positioned, tightening of the locking devices 21 fixes the bridge member 50 in place relative to the plate member 10.

Of course, if desired the bridge member may be attached and/or locked to the plate member 10 prior to insertion. The coupling devices may be coupled to the spinal rods and/or locked into place with respect to the bridge member 50 before or after the position of the bridge member 50 is fixed by tightening of the locking devices 21 of the mounting brackets 20. The surgeon thus has a variety of options in order to accommodate various patients and situations.

Figure 5:
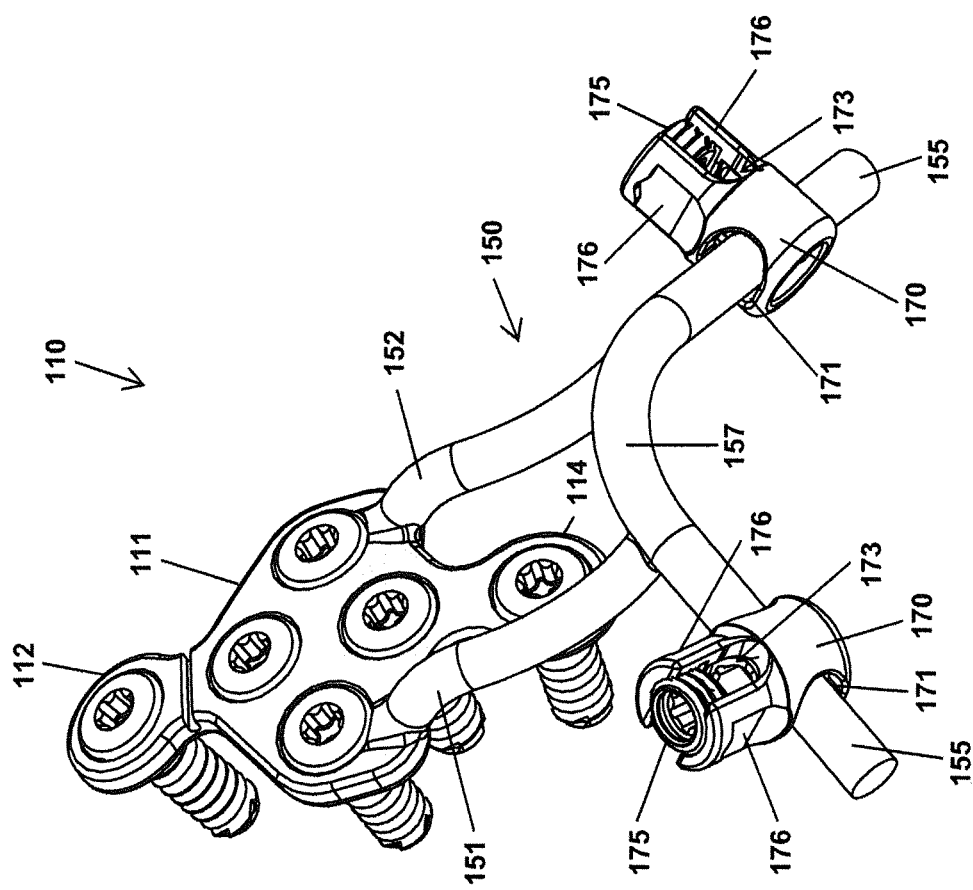
FIG. 5 is a perspective view of a plate device with a fixed bridge portion upon which adjustable coupling members are disposed.
Figure 6:
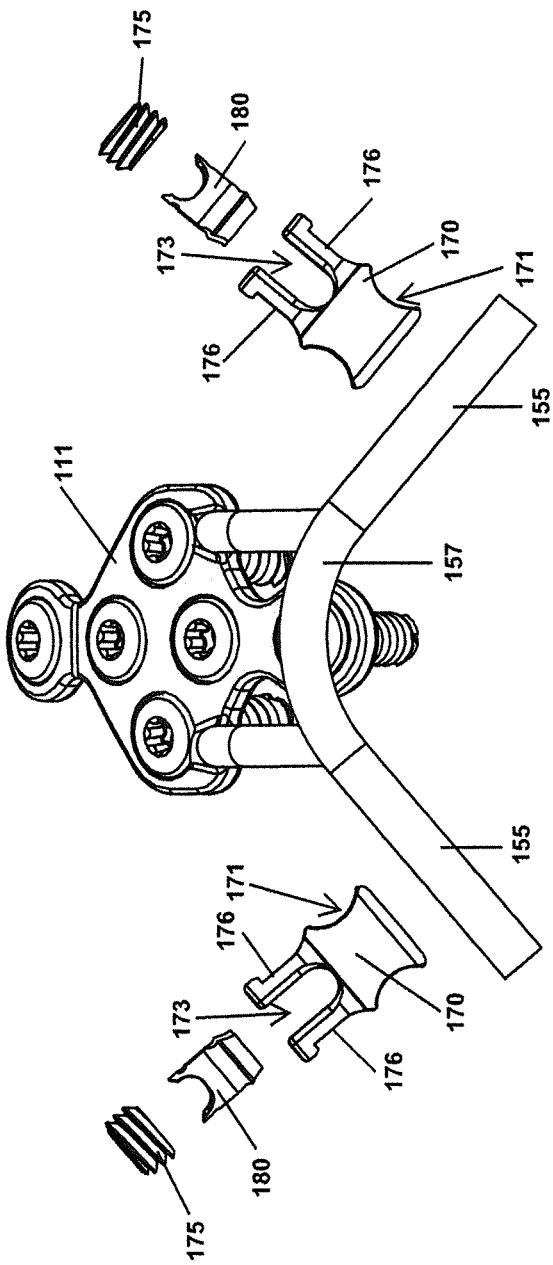
FIG. 6 is an exploded view of the coupling members removed from the device shown in FIG. 5.
Figure 7:
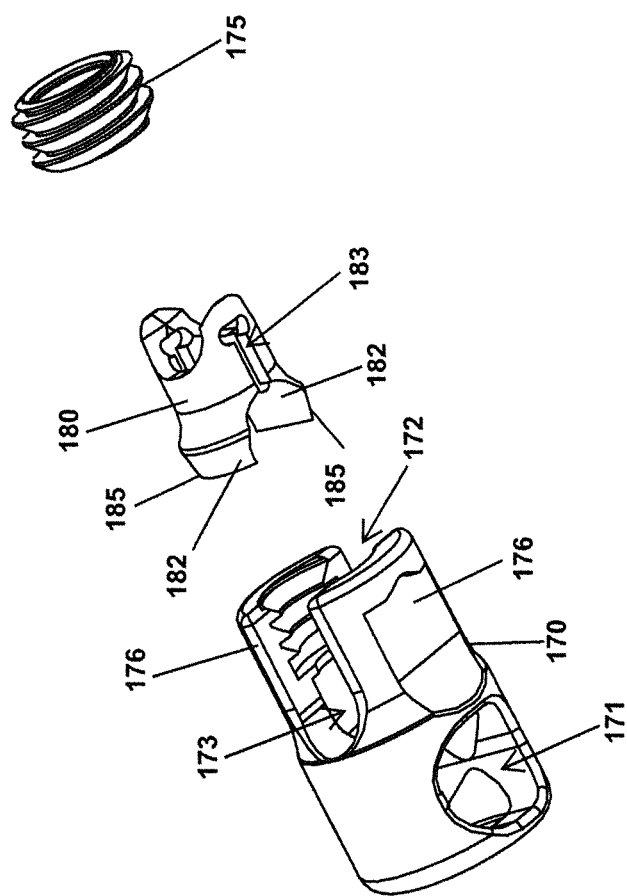
FIG. 7 is an exploded view of the coupling members similar to FIG. 6 showing a compression insert, and a locking cap for being received in a yoke member and fixing a spinal rod relative to the plate member in the yoke member.

Another occipital plate device 110 is shown in FIGS. 5-7. As with the previous embodiment, the device shown in FIGS. 5-7 includes a relatively flat plate body 111 configured to be secured to the patient's skull and secured to a pair of spinal rods through adjustable couple coupling devices 170. The plate body 111 includes a plurality of apertures through which screws 119 or other anchor members may pass in order to anchor the plate 111 to a patient's occiput. The illustrated plate also has grooves or notches 119 at particular points along its surface in order to enhance the bendability of the plate at those points in order to better match the curvature of the skull. The plate may also be cut or broken along grooves 119 to reduce the plate size if upper lobe portion 112 or lower lobe portion 114 are not needed.

Unlike the device of FIG. 1, the plate member shown in FIGS. 5-7 has a fixed bridge portion 150 with integral arms 151 and 152 holding the laterally extending portion 157 at a fixed orientation. A pair of rod receiving coupling devices 170 are slidably and pivotably arranged on lateral arms 155 extending from the bridge portion 150. The lateral arms 155 shown in FIG. 5 are positioned orthogonally to the surface of the plate body 111, so that shifting of the coupling member 170 along the lateral arms 155 changes the position of the coupling member 170 in both the saggital plane and the coronal plane. Furthermore, pivoting of the coupling members 170 along these orthogonal arms will cause the axes of the coupling members' respective rod receiving channels 173 to cant toward or away from one another instead of moving in parallel.

The coupling devices 170 associated with the device 110 shown in FIG. 5 contain throughbores 171 through which the laterally extending arms 155 of bridge portion 150 pass. The illustrated lateral arm portions 55 are generally cylindrical to allow the coupling devices to pivot. The positioning of each coupling device 170 is locked by a set screw 175 or other locking cap that clamps the spinal rod in place within a channel 173 of the coupling device 170. The illustrated laterally extending portion 157 forms an arch 154 between the coupling devices 170 in order to provide clearance for vertebral protuberances and connective tissue of the spine.

The illustrated coupling members 170 of the device 110 shown in FIG. 5 are U-shaped with upright arms 176 that form a channel 173 therebetween sized and shaped to receive a spinal rod. The coupling members 170 also are configured to receive locking members such as set screws 175 that engage the upright arms 176 of the coupling member to secure the spinal rod within the channel 173.

As shown in FIG. 6, the coupling member 170 may also receive a compression insert 180 for assisting in stabilizing and locking the coupling member 170 to the laterally extending arm 155. The compression insert shown in FIG. 6 is inserted through an axial bore 172 through the center of the coupling device and transverse to the rod channel 173, as best shown in FIG. 7. The upper surface of compression insert 180 may be contoured to the surface of the spinal rod. When the insert 180 is sufficiently advanced within the axial bore 172, it compresses against the lateral arm 155 disposed within the transverse throughbore 171, providing a light or provisional locking force to hold the position of the coupling device 170. Positioning the spinal rod within the rod channel 173 and tightening the locking cap 175 firmly fixes the position of the coupling device 170 by pushing down on the compression insert 180, clamping the lateral arm 155 between the lower surface of the transverse throughbore 171 and the bottom surface of the compression insert 180. The illustrated compression insert 180 includes a vertical slit 183 to allow clamp portions 182 to move together to clamp the lateral arm 155 disposed in the transverse throughbore 171 of the coupling member 170. The clamp portions 182 are clamped together when tapered exterior camming surfaces 185 cam against tapered interior surfaces in the axial bore 172 of the coupling member 170.

What is claimed is:

1. A method of fixing an articulated fixation device to a patient, comprising:
    securing a plate member to the patient's skull;
    forming a first adjustable connection between the plate member and a bridge member having a longitudinal axis to allow for relative pivoting therebetween about a first lateral pivot axis extending in the lateral direction transverse to the bridge member longitudinal axis;
    forming a second adjustable connection between the bridge member and a rod coupling device to allow for relative pivoting therebetween about a second lateral pivot axis extending in the lateral direction transverse to the bridge member longitudinal axis that is substantially parallel to the first lateral pivot axis and longitudinally spaced therefrom.

2. The method of claim 1, wherein the first adjustable connection between the plate member and the bridge member is formed prior to or subsequent to securing the plate member to the patient's skull.

3. The method of claim 1, further comprising pivoting the bridge member about the first lateral pivot axis to shift the second adjustable connection in a path transverse to the longitudinal axis and the first and second lateral pivot axes.

4. The method of claim 1, further comprising fixing the plate member and the bridge member against pivoting about the first lateral pivot axis without causing fixing of the bridge member and the rod coupling device against pivoting about the second lateral pivot axis.

5. The method of claim 1, further comprising fixing the bridge member and the coupling device against pivoting about the second lateral pivot axis without causing fixing of the plate member and the bridge member against pivoting about the first lateral pivot axis.

6. The method of claim 1, further comprising fixing a spinal rod to the rod coupling device and fixing the bridge member and the coupling device against pivoting about the second lateral pivot axis with a single locking member.

7. The method of claim 1, further comprising adjusting the position of the bridge member relative to the plate member at the first adjustable connection by shifting the bridge member laterally along the first lateral pivot axis.

8. The method of claim 1 wherein the bridge member is one of a plurality of bridge members having a longitudinal axis, wherein each of the plurality of bridge members has a different size or configuration for accommodating different patients, and further comprising selecting one of the plurality of bridge members based on a given patient.

9. An occipito-cervical fixation system comprising:
    a plate member configured for being secured to a skull;
    an adjustable bridge member separate and distinct from the plate member, and having a longitudinal axis;
    wherein the plate member is configured to form a first adjustable connection with the adjustable bridge member at a first portion of the adjustable bridge member to allow for relative pivoting between the plate member and the adjustable bridge member about a first lateral pivot axis extending in a lateral direction transverse to the adjustable bridge member longitudinal axis; and
    at least one rod coupling device configured to receive a spinal rod and to form a second adjustable connection with the adjustable bridge member at a second portion of the adjustable bridge member spaced from the first portion along the longitudinal axis,
    wherein the second adjustable connection between the adjustable bridge member second portion and the rod coupling device is configured to allow for relative pivoting between the adjustable bridge member second portion and the rod coupling device about a second lateral pivot axis extending in the lateral direction that is substantially parallel to the first lateral pivot axis and longitudinally spaced therefrom.

10. The occipito-cervical fixation system of claim 9, wherein the first adjustable connection includes a first locking mechanism operable to fix the plate member and the adjustable bridge member against pivoting about the first lateral pivot axis, and the second adjustable connection includes a second locking mechanism independently operable from the first locking mechanism to fix the adjustable bridge member and the at least one coupling device against pivoting about the second lateral pivot axis.

11. The occipito-cervical fixation system of claim 9 wherein the adjustable bridge member is one of a set of adjustable bridge members separate and distinct from the plate member, wherein the adjustable bridge members of the set each includes a longitudinal axis and the adjustable bridge members are of a different size or configuration than other ones of the adjustable bridge members in the set.

12. The occipito-cervical fixation system of claim 11, wherein the adjustable bridge members have a length along the longitudinal axis thereof different from the length of other ones of the adjustable bridge members in the set.

13. The occipito-cervical fixation system of claim 11, wherein the adjustable bridge members have a lateral width different from the lateral width of other ones of the adjustable bridge members in the set.

14. An occipito-cervical fixation system comprising:
    a plate member configured for being secured to a skull;
    an adjustable bridge member separate and distinct from the plate member, and having a longitudinal axis;
    wherein the plate member is configured to form a first adjustable connection with the adjustable bridge member at a first portion of the adjustable bridge member to allow for relative pivoting between the plate member and the adjustable bridge member about a first lateral pivot axis extending in a lateral direction transverse to the adjustable bridge member longitudinal axis; and
    at least one rod coupling device configured to receive a spinal rod and to form a second adjustable connection with the adjustable bridge member at a second portion of the adjustable bridge member spaced from the first portion along the longitudinal axis,
    wherein the second adjustable connection between the adjustable bridge member second portion and the rod coupling device is configured to allow for relative pivoting therebetween about a second lateral pivot axis extending in the lateral direction that is substantially parallel to the first lateral pivot axis and longitudinally spaced therefrom,
    wherein the first adjustable connection comprises at least one yoke portion that has an integral, one piece construction with the plate member and includes a laterally extending channel, and at least one laterally extending cross bar of the adjustable bridge member that is configured to be pivotally received in the laterally extending channel.

15. An occipito-cervical fixation system comprising:
    a plate member configured for being secured to a skull;
    an adjustable bridge member separate and distinct from the plate member, and having a longitudinal axis;
    wherein the plate member is configured to form a first adjustable connection with the adjustable bridge member at a first portion of the adjustable bridge member to allow for relative pivoting between the plate member and the adjustable bridge member about a first lateral pivot axis extending in a lateral direction transverse to the adjustable bridge member longitudinal axis; and at least one rod coupling device configured to receive a spinal rod and to form a second adjustable connection with the adjustable bridge member at a second portion of the adjustable bridge member spaced from the first portion along the longitudinal axis, wherein the second adjustable connection between the adjustable bridge member second portion and the rod coupling device is configured to allow for relative pivoting therebetween about a second lateral pivot axis extending in the lateral direction that is substantially parallel to the first lateral pivot axis and longitudinally spaced therefrom, wherein the second adjustable connection comprises a laterally extending through opening of the at least one rod coupling device that extends in a lateral direction, and the adjustable bridge member has a longitudinally extending portion and a lateral arm extending laterally therefrom that is configured to be pivotally received in the laterally extending through opening.

16. An occipito-cervical fixation system comprising:

a plate member configured for being secured to a skull;

an adjustable bridge member separate and distinct from the plate member, and having a longitudinal axis;

wherein the plate member is configured to form a first adjustable connection with the adjustable bridge member at a first portion of the adjustable bridge member to allow for relative pivoting between the plate member and the adjustable bridge member about a first lateral pivot axis extending in a lateral direction transverse to the adjustable bridge member longitudinal axis; and at least one rod coupling device configured to receive a spinal rod and to form a second adjustable connection with the adjustable bridge member at a second portion of the adjustable bridge member spaced from the first portion along the longitudinal axis, wherein the second adjustable connection between the adjustable bridge member second portion and the rod coupling device is configured to allow for relative pivoting therebetween about a second lateral pivot axis extending in the lateral direction that is substantially parallel to the first lateral pivot axis and longitudinally spaced therefrom, wherein the at least one rod coupling device comprises a pair of rod coupling devices each including a laterally extending through opening that extends in a lateral direction, and the adjustable bridge member includes a pair of laterally extending arms configured to be pivotally received in the laterally extending through openings.

17. The occipito-cervical fixation system of claim 16, wherein the adjustable bridge member further includes an arched portion interconnecting the laterally extending arms having a generally inverted U-shaped configuration for providing clearance for avoiding contact with the spine.

* * * * *